United States Patent [19]

Pansiera

[11] Patent Number: 4,681,097
[45] Date of Patent: Jul. 21, 1987

[54] ORTHOPEDIC BRACE

[76] Inventor: Timothy T. Pansiera, 1335 NE. 28th St., Pompano Beach, Fla. 33064

[21] Appl. No.: 824,284

[22] Filed: Jan. 23, 1986

[51] Int. Cl.$^4$ .............................................. A61F 5/01
[52] U.S. Cl. .................................. 128/77; 128/80 C; 128/80 F; 128/88
[58] Field of Search ............... 128/77, 88, 80 R, 80 C, 128/80 F

[56] References Cited

U.S. PATENT DOCUMENTS

| 4,255 | 11/1845 | Hoar | 128/88 |
|---|---|---|---|
| 21,872 | 10/1858 | Bunce | 128/88 |
| 575,199 | 1/1897 | Autenrieth | 128/88 |
| 618,097 | 1/1899 | Hill | 128/88 |
| 1,340,630 | 5/1920 | Maddox | 128/88 |
| 1,374,177 | 4/1921 | Barry | 128/88 |
| 1,939,097 | 12/1933 | Bauman | 128/80 F |
| 2,144,641 | 1/1939 | Snyder | 128/80 C |
| 3,785,372 | 1/1974 | Craig | 128/80 C |
| 3,844,279 | 10/1974 | Konvalin | 128/80 F |
| 4,408,600 | 10/1983 | Davis | 128/80 R |

FOREIGN PATENT DOCUMENTS

| 35576 | 3/1909 | Austria | 128/88 |
|---|---|---|---|
| 516989 | 4/1921 | France | 128/88 |
| 541973 | 4/1956 | Italy | 128/80 F |
| 125511 | 4/1919 | United Kingdom | 128/88 |

Primary Examiner—Clyde I. Coughenour
Attorney, Agent, or Firm—M. K. Silverman

[57] ABSTRACT

The invention relates to an orthopedic brace having a U-shaped upper frame proportioned to abut and support the posterior, proximal area of the leg including means for selectably changing its transverse width. Also provided is an upper pad position adjustment element press-fittable attached to the transverse width-changing means in more than one position relative to the major axis of the upper frame. Secured to the upper pad position adjustment element is a proximal posterior support utilizing means such as velcro for detachable attachment. There is also provided a proximal anterior pad having a smaller dimension than the proximal posterior pad and strap means for mechanically joining said anterior pad and the posterior pad support. The strap means further comprising means for adjusting the pressure of the anterior and posterior pads upon the upper leg of the user. A near mirror-image set of lower leg elements is included with a hinge means for selectably changing and locking the position of said upper frame and its associated pads and straps relative to the lower frame and its associated elements.

3 Claims, 10 Drawing Figures

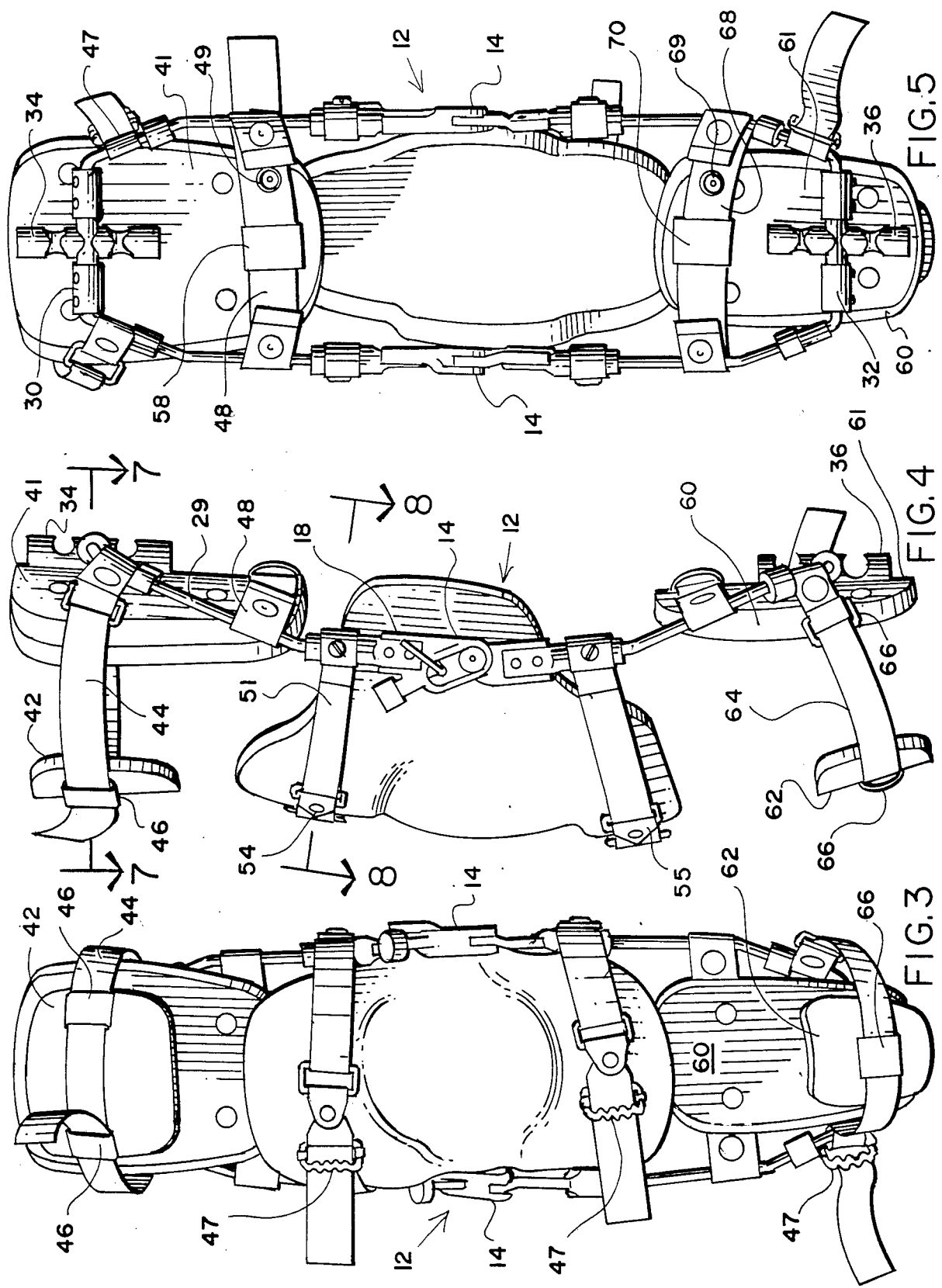

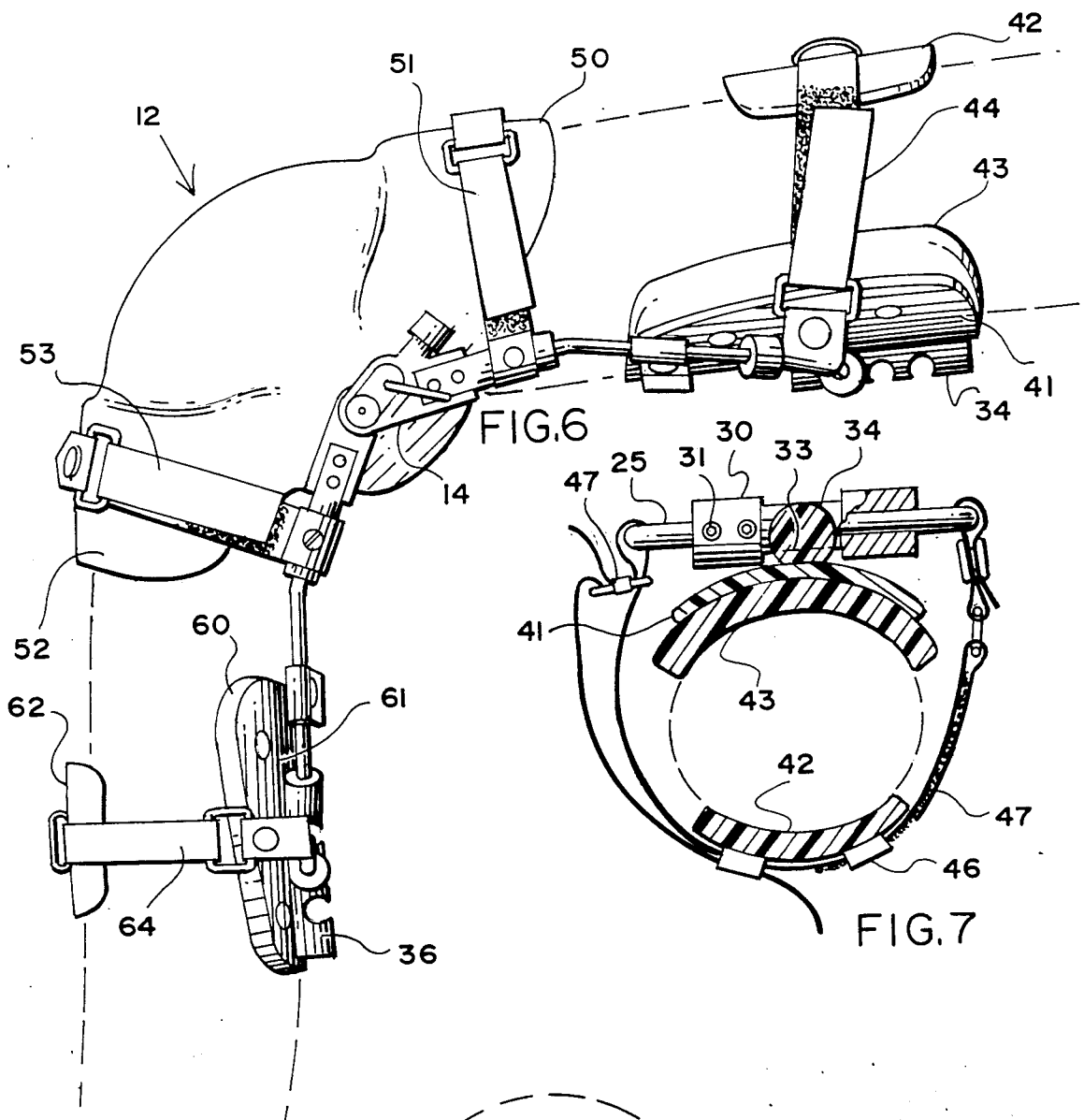
FIG.6
FIG.7
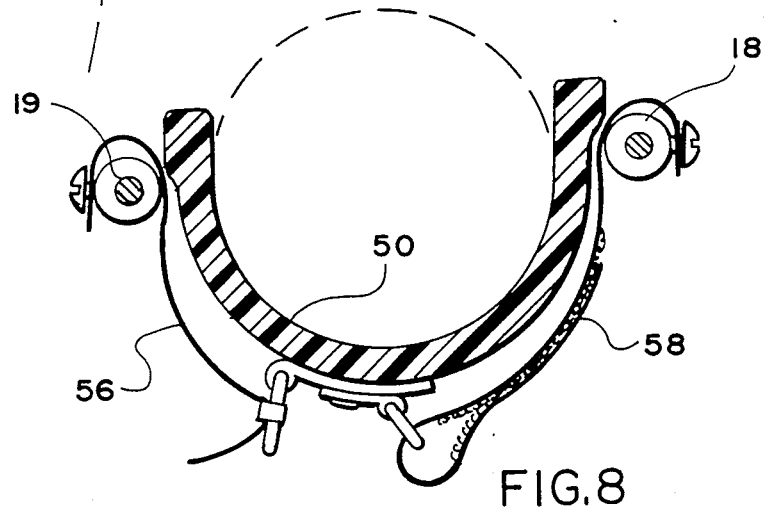
FIG.8

ORTHOPEDIC BRACE

BACKGROUND OF THE INVENTION

A need has long existed for an Orthopedic Brace for the distal and proximal areas of the legs suitable for limiting the motion of the knee following certain post-operative procedures and, as well, as a treatment of other types of orthopedic dysfunctions.

A problem in the prior art has been the need to separately and individually fit each knee brace wearer with a knee brace having a customized proximal and distal length, an adjustable transverse width at both the proximal and distal end of the brace, and a customized system of anterior and posterior support pads both above and below the knee.

Further, different braces have required different forms of hinge couplings at the point of joinder between the upper and lower leg portions thereof.

The existence of so many variables in the construction of orthopedic braces has added substantially to the cost of such braces in that, as above noted, the construction of most leg braces for the treatment of post-operative and other dysfunctions has become a customized patient-by-patient situation.

The present invention seeks to address the above problems of construction and cost through the presentation of a so-called Universal Brace using a common "skeleton" which, through the adjustment of certain elements, straps and loops, can be adapted to virtually every leg anatomy and orthopedic need situation. Through such an approach, there is provided a structure for limiting the motion of the knee within a plurality of positions and, as well, a means for providing a variety of anterior and posterior upper and lower leg pressure points. To the knowledge of the inventor, there does not exist prior art bearing upon the novelty of the present invention.

SUMMARY OF THE INVENTION

The invention relates to an orthopedic brace having a U-shaped upper frame proportioned to abut and support the posterior, proximal area of the leg, said upper frame comprising means for selectably changing its transverse width. Further provided is an upper pad position adjustment element press-fittable attached to said transverse width-changing means in more than one position relative to the major axis of said upper frame. Secured to said upper pad position adjustment element is a proximal posterior support utilizing means such as velcro for such detachable attachment. There is further provided a proximal anterior pad having a smaller dimension than said proximal posterior pad. Further provided are strap means for mechanically joining said anterior pad and said posterior pad support, said strap means further comprising means for adjusting the pressure of said anterior and posterior pads upon the upper leg of the user.

There is furnished a near mirror-image set of lower leg elements including the above-mentioned U-shaped frame, a lower pad position adjustment element, a distal posterior support, a distal posterior pad detachably attachable to said distal pad support, a distal anterior pad, and strap means for mechanically joining said distal anterior pad and said distal posterior pad support, including pressure adjustment means therefor.

A hinge means is provided for selectably changing and locking the position of said upper frame and its associated pads and straps relative to said lower frame and its associated elements.

It is therefore an object of the present invention to provide a so-called universal orthopedic brace capable of adjustment into a number of different lengths and transverse widths and, as well, having a capability for ready replacement of the various pressure pads and, having control of pressure areas against the proximal leg, distal leg, upper knee, lower knee, at both the posterior and anterior thereof, this including both the right and left leg interchangably. Yet further objects and advantages of the present invention will become apparent from hereinafter set forth detailed description of the invention, the drawings, and claims appended herewith.

BRIEF DESCRIPTION OF THE DRAWINGS

FIG. 3 is a front perspective view of the brace.

FIG. 4 is a side perspective view of the brace.

FIG. 5 is a rear perspective view of the brace.

FIG. 6 is a side, enlarged, operational view of the brace showing the leg of a user in phantom.

FIG. 7 is a cross-sectional radial view taken along Line 7—7 of FIGS. 4 and 6.

FIG. 8 is a cross-sectional radial view taken along Lines 8—8 of FIGS. 4 and 6.

DETAILED DESCRIPTION OF THE INVENTION

Figure 1:
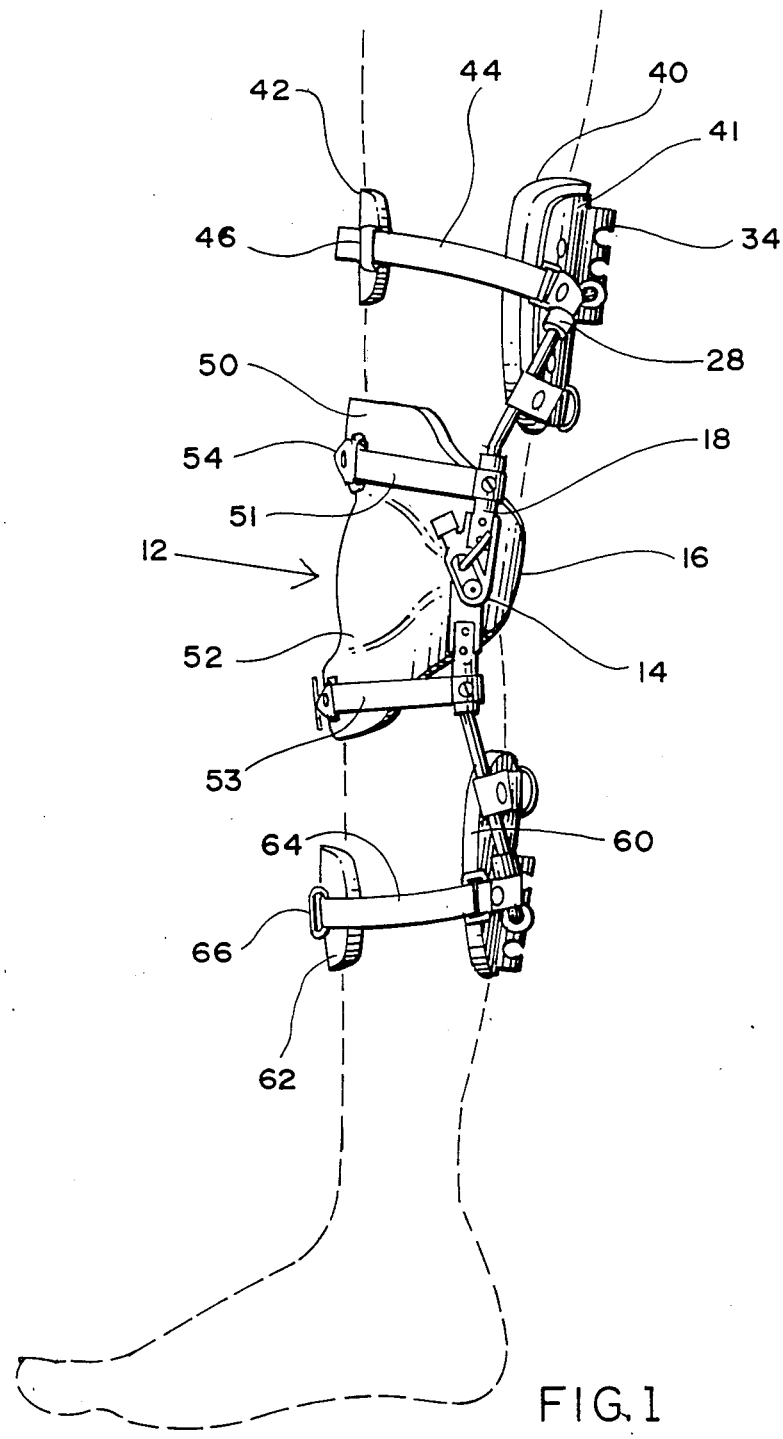
FIG. 1 is a perspective view of the present inventive orthopedic brace showing the leg of a user in phantom.
Figure 2:
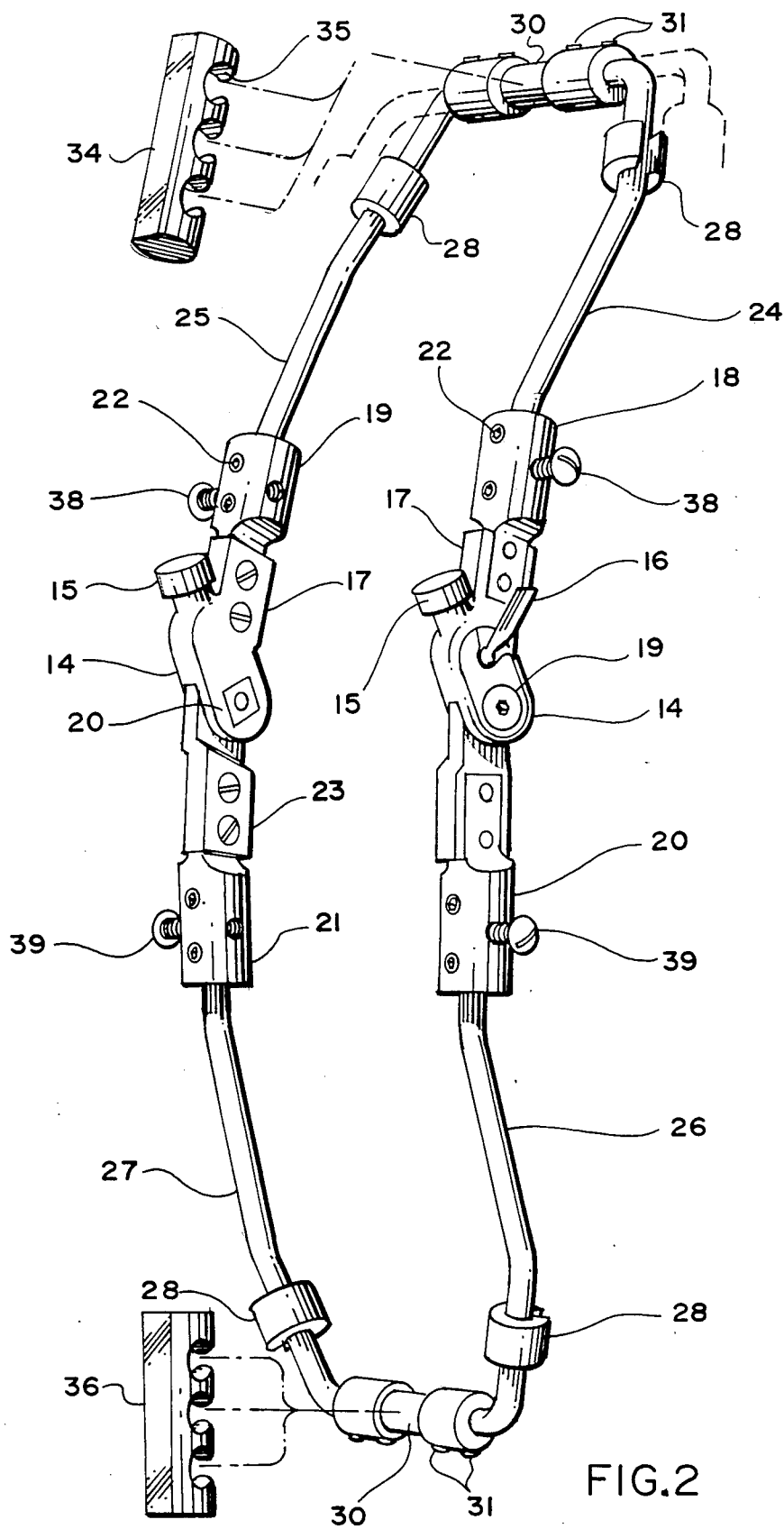
FIG. 2 is a perspective, partial exploded view of the skeleton of the inventive brace.
Figure 9:
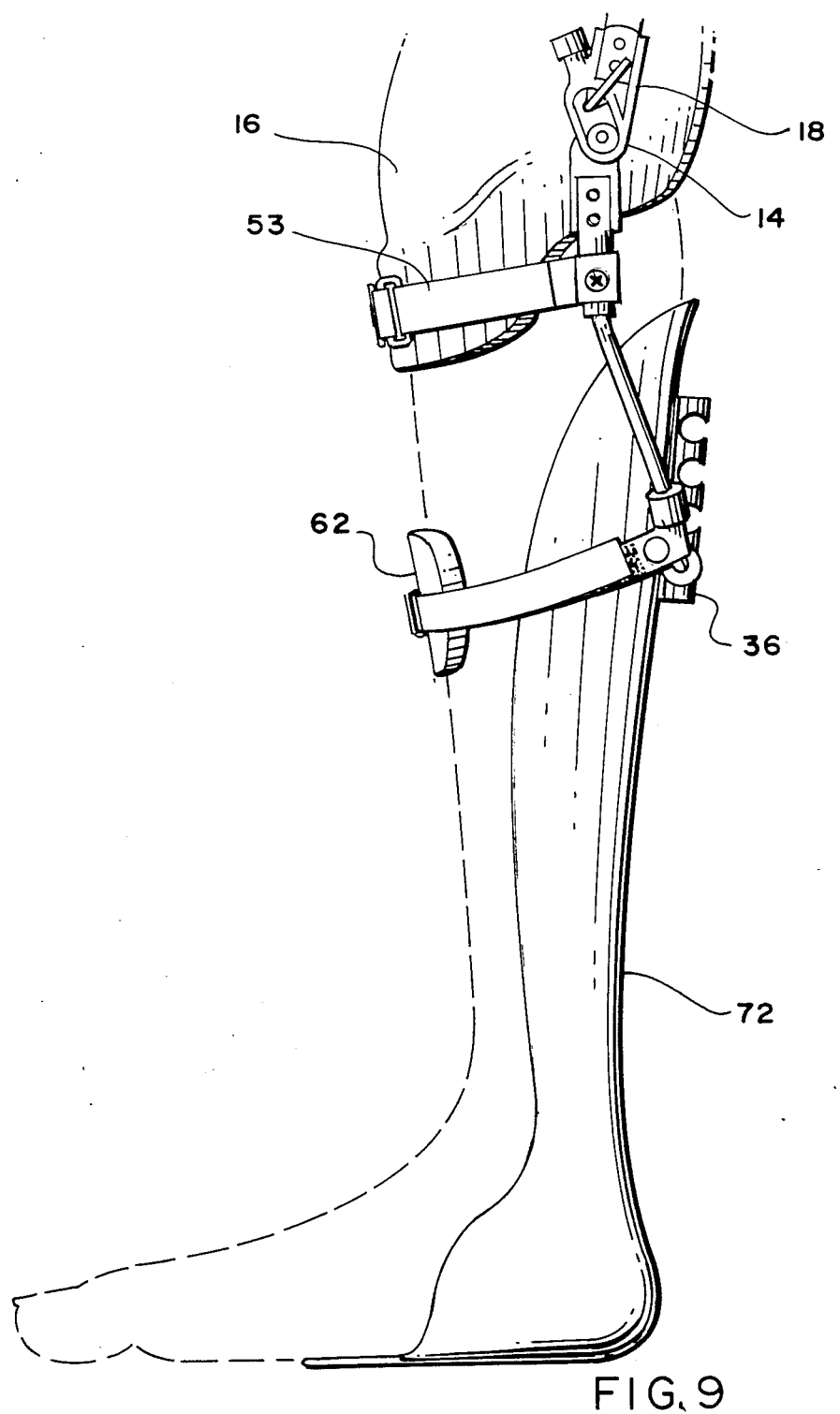
FIG. 9 is a view, similar to the perspective view of FIG. 1, however, showing an optional heel extension element of the brace.

With reference to the views of FIGS. 1 and 2, there is shown the present inventive Auto Stop Anterior/Posterior knee brace. The inventive brace comprises a centrally disposed hinge means 14 which includes a control element 16 by which the position of the upper member of the hinge means relative to the lower member and, thereby, the position of proximal joint couplings 18 and 19 relative to the position of distal joint couplings 20 and 21 is thereby determined.

A suitable structure for hinge means 14 is more particularly described in my U.S. Pat. No. 4,502,472 entitled hinge means for orthopedic brace. However, it is to be appreciated and understood that other hinge means as, for example, drop-step, polycentric, and other state of the art orthopedic hinges may be used. The desired arc of movement between the upper and lower areas of the brace is indicated by the curvilinear arrows shown in FIG. 2.

The underlying concept of the present invention is that of a brace which is adjustable in both the longitudinal (lengthwise) direction, as well as transversly. In addition, posterior pads (later described) are adapted for removability from the brace proper thereby facilitating easy removal, interchangability, and replacement of posterior pads from the brace skeleton. In addition, the above-referenced hinge means 14 provides to the present brace a capability of lock-step adjustability of the upper assembly of the brace relative to the lower assembly of the brace.

With regard to the specific hardware which comprises the frame of the present inventive universal brace, there is shown in FIG. 2 upper hinge coupling extension 17 which is fixedly secured to proximal joint couplings 18 and 19. As noted in FIG. 2, Allen-head screws 22 enable connection of right proximal side rod 24 to right proximal joint coupling 18, while left proximal side rod 25 is connected to left proximal joint coupling 19 by means of said Allen-head screws 22.

Strap screw 38, disposed upon the proximal joint couplings, functions only in connection with the proximal knee straps which are later described.

Upon proximal side rods 24 and 25 are strap retainers 28, the function of which is to assure the proper positioning of anterior velcro strap 44. See FIG. 1.

Also shown in FIG. 2, in phantom, is the range of adjustability of the upper ends of proximal side rods 24 and 25 in the transverse direction. The degree of transverse adjustability of the proximal side rods 24 and 25 is controllable by selectable use of said Allen-head screws 31.

It is to be appreciated that said side rods do not touch the leg of the user.

Further shown at the top of FIG. 2 is proximal pad adjustment element 34 which, as shown therein, is provided with a plurality of hemispherical recesses 35, the purpose of which is to engage proximal pivot coupling 30. It is thereby to be appreciated that the top of FIG. 2 is an exploded triple path view of proximate pad adjustment element 34 relative to proximal pivot coupling 30, i.e., each of the three possible positions of the recesses 35 of proximate pad adjustment element 34 are shown. Thereby, it may be appreciated that the longitudinal length of the skeleton of the brace may be selectively extended or reduced dependent upon the choice of recess 35 of pad adjustment element 34 which is employed in frictional engagement with pivot coupling unit 30.

With respect to the lower half of the skeleton of the brace shown in FIG. 2, it is to be appreciated that the lower, or distal, portion thereof is essentially a mirror image of the top, or proximal, end thereof.

With reference to FIGS. 14 and 16, there is shown the anatomical interaction between the leg of the user and the present inventive universal brace. More particularly, there is shown a plurality of pads which are connected by a variety of strap/loop arrangements to the above-described skeleton of the brace. More specifically, with reference to the upper portion of FIGS. 1, 4 and 6, there is shown the proximal portion of the leg and, more specifically, there is shown said proximal pad adjustment element 34 and, integrally bonded thereto, proximal, posterior hard curviplaner element 41 which is integrally bonded to said pad adjustment element 34.

With further reference to FIGS. 1, 4 and 6, there is shown posterior proximal pad 41 which is a soft removable pad which is connected to hard curviplaner element 41 by a velcro attachment means 43 which is more particularly shown in the radial cross-sectional view of FIG. 7. Therein may also be seen anterior proximal pad 42 including loops 46 and anterior velcro strap 44 which connects anterior proximal pad 42 to the upper portion of the present brace. The provision of velcro attachment means 43 makes possible easy removability and/or replacement of posterior proximal pad 40 as it becomes worn or replacement thereof otherwise becomes necessary by reason of the medical needs of the patient.

With further reference to FIG. 7, it is noted that velcro is required on one side of the anterior strap 44 in order to assure stability of the strap 44 relative to the anterior proximal pad 42. Snap 45 makes possible the complete removal of strap 44 and pad 42, if required, during fitting of the patient. Slide buckle 47 (at the left of FIG. 7) facilitates small adjustments of pressure of the anterior proximal pad 42 relative to the front of the user's leg.

At the level of the proximal joint couplings 18 and 19 is located proximal knee pad 50 and strap 51 which serves to position proximal knee pad 50 relative to the proximal joint couplings 18 and 19. See FIGS. 1, 4, 6 and 8.

It is noted in FIG. 8, strap 51 is provided with velcro which, in combination with proximal buckle 54, assists in the polar securement of proximal knee pad 50 relative to the upper knee area of the user. Also shown in FIGS. 4 and 8 is slide buckle strap 56 to enable the application of considerable pressure, as needed, to the upper knee area of the user, while the function of strap 51 is primarily that of assuring proper position of the proximal upper knee pad 50 relative to the upper knee area.

As may be appreciated from the perspective view of FIG. 1, the lower or distal portion of the brace is substantially identical to the top or proximal portion thereof. More particularly, the distal portion is similarly provided with a system of lower area knee pads which are substantially a mirror image of the above-discussed system of upper knee area elements described with reference to FIG. 8.

Similarly, and with particular reference to FIGS. 1, 4 and 6, there is shown posterior distal pad 60, distal adjustment strap 64, and anterior distal pad 62. Pads 60 and 62, while slightly smaller in their dimensions, are positioned and adjusted in the same fashion as is above described with reference to proximal pads 40 and 42. Most importantly, posterior distal pad 62 is selectively detachable from hard curviplaner element 61 thru velcro means similar to velcro means 43 shown in FIG. 7. Accordingly, through the use of such velcro means, both the posterior proximal and distal pads 40 and 60 respectively may be removed or changed as needed without otherwise changing the overall brace structure. Similarly, it is to be appreciated that the anterior proximal and distal pads 42 and 62 respectively may be readily replaced by sliding them off of straps 44 or 64 respectively, upon loops 46 and 66 which are integral to the anterior pads 42 and 62 respectively.

With reference to FIG. 5, it is to be further noted that the position of the posterior pads 40 and 60 respectively is controlled through two major pivot points. The first being the intersection between pivot coupling 30 and pad adjustment element 34. The second being proximal contact loop 58 which is integrated with curviplaner element 41 in combination with proximal tension strap 48 on the upper leg.

The respective upper and lower contact pads 58 and 70 are bonded to hard curviplaner posterior pads support elements 41 and 61 respectively. Thereby, a large measure of control of position and range of movement of the proximal and distal posterior pads is achieved. The degree of tension of straps 48 and 68 is controlled by the position of snaps 49 and 69 respectively which are used to control the degree of resilient tension exerted by straps 48 and 68 respectively against elements 41 and 61 respectively.

In an alternative and further embodiment of the present invention, distal side rods 26 and 27 may be provided with heel extension elements serving to control the range of motion of the ankle and foot relative to the distal portion of the inventive brace.

Figure 10:
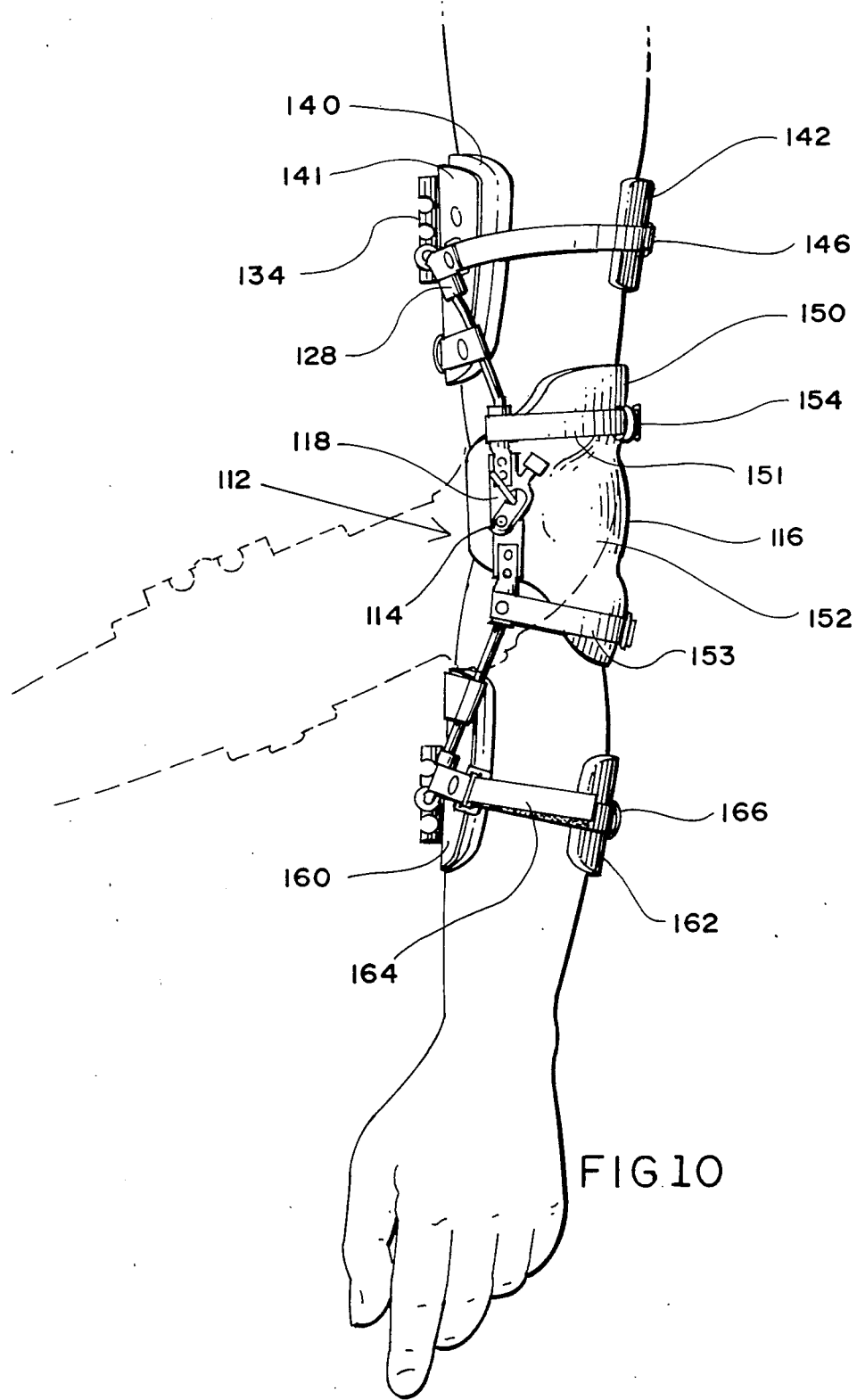
FIG. 10 is a perspective view of an embodiment of the inventive brace useable in connection with the arm.

Shown in FIG. 10 is an embodiment of the present invention demonstrating the usage thereof in connection with an arm.

While there has been herein shown and described the preferred embodiments of the present invention, it is to be understood the invention may be embodied otherwise than is herein illustrated and described and that in said embodiments, certain changes in the detailed construction, and in the form and arrangement of parts may be made without departing from the underlying idea or principles of this invention within the scope of the appended claims.

Having thus described my invention what I claim as new, useful and non-obvious and, accordingly, secure with Letters Patent of the United States is:

1. An orthopedic brace, comprising:
   (a) a U-shaped upper frame proportioned to a posterior, proximal area of a body limb, said upper frame comprising means for selectably changing the transverse width thereof, such frame having a major axis;
   (b) an upper pad position adjustment element press-fittably rotatably attachable to said transverse width changing means, in more than one position relative to the major axis of said upper frame;
   (c) a proximal posterior pad support secured to said upper pad position adjustment element;
   (d) a proximal posterior pad detachably attachable to said proximal posterior pad support;
   (e) a proximal anterior pad;
   (f) strap means for mechanically joining said anterior proximal pad and said posterior pad supports, said strap means further comprising means for adjusting the direction and pressure of said posterior pad upon the upper area of the limb of the user;
   (g) a U-shaped lower frame proportioned to a posterior distal area of the limb, said lower frame comprising means for selectably changing the transverse width thereof, said frame having a major axis;
   (h) a lower pad position adjustment element press-fittably rotatably attachable to said transverse width-changing means in more than one position relative to the major axis of said lower frame;
   (i) a distal posterior pad support secured to said lower pad position adjustment element;
   (j) a distal posterior pad detachably attachable to said distal posterior pad support;
   (k) a distal anterior pad;
   (l) strap means for mechanically joining said anterior distal anterior pad and said distal pad support, said strap means further including means for adjusting the pressure of said anterior and posterior distal pads upon the lower area of the limb of the user;
   (m) a hinge means for selectably changing and locking the position of said upper frame and its attendant elements relative to said lower frame and its attendant elements; and
   (n) anterior joint pad and straps therefore joining said new pad to said U-shaped frames above and below said hinge means.

2. The brace as recited in claim 1 in which said body portion comprises a leg.

3. The brace as recited in claim 1 in which said body portion comprises an arm.

* * * * *